US00PP21567P3

(12) United States Plant Patent
Zaiger et al.

(10) Patent No.: US PP21,567 P3
(45) Date of Patent: Dec. 14, 2010

(54) PEACH TREE NAMED 'SUNNIRICH'

(50) Latin Name: *Prunus persica*
Varietal Denomination: Sunnirich

(76) Inventors: Gary Neil Zaiger, 1907 Elm Ave., Modesto, CA (US) 95358; Leith Marie Gardner, 1207 Grimes Ave., Modesto, CA (US) 95358; Grant Gene Zaiger, 4005 California Ave., Modesto, CA (US) 95358

( * ) Notice: Subject to any disclaimer, the term of this patent is extended or adjusted under 35 U.S.C. 154(b) by 169 days.

(21) Appl. No.: 12/378,272

(22) Filed: Feb. 13, 2009

(65) Prior Publication Data

US 2010/0212052 P1 Aug. 19, 2010

(51) Int. Cl.
*A01H 5/00* (2006.01)

(52) U.S. Cl. ..... Plt./197

(58) Field of Classification Search ..... Plt./197
See application file for complete search history.

(56) References Cited

U.S. PATENT DOCUMENTS

PP2,964 P * 1/1970 Merrill ..... Plt./198
PP3,022 P * 2/1971 Merrill ..... Plt./198
PP7,290 P * 8/1990 Zaiger et al. ..... Plt./197
PP11,090 P * 10/1999 Zaiger et al. ..... Plt./197
PP17,016 P3 * 8/2006 Gerdts et al. ..... Plt./197

* cited by examiner

*Primary Examiner*—Wendy C. Haas

(57) ABSTRACT

A new and distinct variety of Peach tree (*Prunus persica*). The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. The tree being a regular and productive bearer of large size fruit.
2. The tree with vigorous, upright growth.
3. Producing fruit with a high degree of attractive orange-red skin color.
4. Producing fruit with good storage and shipping quality.
5. Fruit with a mild, sweet, low-acid flavor and very good eating quality.

1 Drawing Sheet

Botanical classification: *Prunus persica.*

STATEMENT REGARDING FEDERALLY SPONSORED RESEARCH AND DEVELOPMENT

Not applicable.

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of peach tree was originated and asexually reproduced by us in our experimental orchard located near Modesto, Stanislaus County, Calif.

PRIOR VARIETIES

Among the existing varieties of peach trees, which are known to us, and mentioned herein, are 'Country Sweet' (U.S. Plant Pat. No. 11,090), 'Rich Lady' (U.S. Plant Pat. No. 7,290), 'O'Henry' (U.S. Plant Pat. No. 2,964), 'June Lady' (U.S. Plant Pat. No. 3,022) and the proprietary peach seedlings selections with the field identification numbers '178LE186' and '11GA1023'.

ORIGIN OF THE VARIETY

The new and distinct variety of peach tree (*Prunus persica*) was developed by us in our experimental orchard located near Modesto, Calif. from seed of a first generation cross between our two proprietary seedling '178LE186' and '11GA1023'. The seed parent (178LE186) originated from a cross between the peaches 'Country Sweet' (U.S. Plant Pat. No. 11,090) and 'Rich Lady' (U.S. Plant Pat. No. 7,290). The pollen parent (11GA1023) originated from a cross between the peaches 'O'Henry' Peach (U.S. Plant Pat. No. 2,964) and 'June Lady' (U.S. Plant Pat. No. 3,022). A large number of seed from this first generation cross were grown and budded to older trees of 'Nemaguard' Rootstock (non-patented), to accelerate rapid fruit production for evaluation. Under close observation, one such seedling, which is the present variety, exhibited desirable tree and fruit characteristic and was selected for asexual propagation and commercialization in 1998.

ASEXUAL REPRODUCTION OF THE VARIETY

Asexual reproduction of the new and distinct variety of peach tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The present new variety of peach tree (*Prunus persica*) is of large size, vigorous upright growth and a productive and regular bearer of large size, yellow flesh, clingstone fruit with mild, sweet, low acid flavor with very good eating quality. The fruit is further characterized by having an attractive orange-red skin color, firm, yellow flesh, large in size and being relatively uniform in size throughout the tree. In comparison to the proprietary seed parent (178LE186) the fruit of the new variety is larger in size and is approximately 20 days later in maturity. In comparison to the proprietary pollen parent (11GA1023), the fruit of the new variety has low acid compared to acidic, is more uniform in size throughout the tree and is approximately 22 days earlier in maturity.

PHOTOGRAPH OF THE VARIETY

The accompanying color photographic illustration shows typical specimens of the foliage and fruit of the present new peach variety. The illustration shows the upper and lower surface of the leaves, an exterior and sectional view of a single fruit divided in its suture plane to show flesh color, pit cavity and the stone remaining in place. The photographic illustration was taken shortly after being picked (shipping ripe) from a 10 year old tree and the colors are as nearly true as is reasonably possible in a color representation of this type.

DESCRIPTION OF THE VARIETY

The following is a detailed botanical description of the new variety of peach tree, its flowers, foliage and fruit, as based on observations of 10 year old specimens grown near Modesto, Calif., with color in accordance with Munsell Book of Color.

Tree:

*Size.*—Large, normally pruned to 3 to 3.5 meters in height for economical harvesting of fruit. Average spread 3 meters.

*Vigor.*—Vigorous, growth of 1.5 to 2 meters in height the first growing season. Varies with soil type, fertility of soil and climatic conditions.

*Form.*—Upright, usually pruned to vase shape.

*Branching habit.*—Crotch angle approximately 35°, increases with heavy crop load.

*Productivity.*—Productive, fruit thinning and spacing necessary for desired market size.

*Bearer.*—Regular, adequate set for 8 consecutive years. No alternate bearing observed.

*Fertility.*—Self fertile.

*Density.*—Medium dense, usually pruned to vase shape to allow more sunlight to center of tree to enhance fruit color and health of fruit wood.

*Hardiness.*—Hardy in all stone fruit growing areas of California. Tree grown in USDA Hardiness Zone 9. Winter chilling requirement approximately 900 hours at or below 45° F.

Trunk:

*Size.*—Medium. Average circumference 43.2 cm at 30.5 cm above ground on a 10 year old tree.

*Stocky.*—Medium stocky.

*Texture.*—Medium shaggy, roughness increase with age.

*Color.*—Varies from 10YR 3/2 to 2.5Y 3/4.

Branches:

*Size.*—Medium. Average circumference 18.0 cm at 1.3 meters above ground.

*Surface texture.*—New growth relatively smooth. Mature growth medium rough, roughness increases with age of growth.

*Lenticels.*—Medium to large. Average length 3.2 mm. Average width 2.2 mm. Color 10YR 5/8 to 10YR 5/10. Average number 22 in a 25.8 sq cm area.

*Color.*—New growth varies from 5GY 6/6 to 7.5YR 4/4. Mature growth varies from 10YR 3/4 to 2.5Y 3/4, varies with age of growth.

Leaves:

*Size.*—Large. Average length 165.9 mm. Average width 37.8 mm.

*Form.*—Lanceolate.

*Apex.*—Acuminate.

*Base.*—Cuneate.

*Margin.*—Crenate.

*Thickness.*—Medium.

*Surface texture.*—Upper surface relatively smooth, slightly indented over midrib and leaf veins, glabrous. Lower surface relatively smooth except for small ridges created by midrib and pinnate venation, glabrous.

*Petiole.*—Average length 9.7 mm. Average width 1.4 mm. Color varies from 2.5GY 5/6 to 5GY 4/6. Longitudinally grooved. Surface — glabrous.

*Stipules.*—Average length 8.7 mm. Average number 2. Margin — pectinate. Color 5GY 6/10.

*Glands.*—Type — reniform. Size — medium. Average length 1.2 mm. Average diameter 0.8 mm. Number — average number 4, varies from 3 to 5. Located primarily on base of leaf blade, and upper portion of petiole. Color varies from 5GY 5/6 to 5GY 4/6.

*Color.*—Upper surface varies from 5GY 4/8 to 5GY 3/6. Lower surface varies from 5GY 5/6 to 5GY 4/6.

*Midrib color.*—Varies from 2.5GY 7/8 to 2.5GY 6/6.

Flower buds:

*Size.*—Large. Average length 18.4 mm. Average diameter 10.4 mm.

*Hardiness.*—Hardy with respect to California winters.

*Form.*—Conical, becoming elongated before opening.

*Pedicel.*—Average length 4.9 mm. Average width 1.2 mm. Color varies from 2.5GY 6/6 to 2.5GY 5/8.

*Color.*—Varies from 7.5RP 8/6 to 7.5RP 7/8.

Flowers:

*Blooming period.*—Date of First Bloom Mar. 3, 2008. Date of Petal Fall Mar. 12, 2008, varies slightly with climatic conditions.

*Size.*—Large, showy. Average height 18.8 mm. Average diameter 42.1 mm.

*Petals.*—Number — 5, alternately arranged to sepals. Size — large. Average length 21.7. mm. Average width 19.8 mm. Form — orbicular, narrows at point of attachment. Margin — sinuate. Both upper and lower surfaces glabrous. Color varies from 5RP 8/6 to 7.5RP 9/2.

*Sepals.*—Number — 5, alternately arranged to petals. Size — medium. Average length 6.6 mm. Average width 6.2 mm. Shape — ovate, apex rounded. Margin — entire. Upper surface — glabrous. Lower surface — pubescent. Color — upper surface varies from 2.5GY 5/6 to 2.5GY 5/8. Lower surface varies from 2.5R 3/4 to 2.5R 2/4.

*Stamens.*—Average number — 39. Filament color varies from 5RP 9/2 to 5RP 8/6. Anther color varies from 2.5Y 8/6 to 10R 4/8.

*Pollen.*—Self fertile. Color varies from 2.5Y 7/12 to 2.5Y 6/10.

*Pistil.*—Number — normally one. Surface — pubescent. Average length 17.9 mm. Position of stigma average of 1.3 mm above anthers. Color varies from 7.5Y 8.5/4 to 10Y 8/6.

*Fragrance.*—Moderate aroma.

*Color.*—Varies from 5RP 8/6 to 5RP 7/8.

*Number flowers per flower bud.*—One.

*Pedicel.*—Average length 5.4 mm. Average width 1.2 mm. Color varies from 2.5GY 6/6 to 2.5GY 5/8.

Fruit:

*Maturity when described.*—Firm ripe.

*Date of first picking.*—Jul. 1, 2008.

*Date of last picking.*—Jul. 8, 2008, varies slightly with climatic conditions.

*Size.*—Large. Average diameter axially 68.7 mm. Average transversely in suture plane 80.4 mm. Average weight 255.6 grams; varies slightly with fertility of the soil, amount of thinning and climatic conditions.

*Form.*—Globose.

*Suture.*—Nearly smooth, extends from base to apex.

*Ventral surface.*—Very slightly lipped, nearly smooth.

*Apex.*—Slightly retuse.

*Base.*—Slightly retuse.

*Cavity.*—Rounded to slightly elongated in suture plane. Average depth 5.8 mm. Average diameter 16.8 mm.

Stem:

*Size.*—Medium. Average length 9.9 mm. Average diameter 3.4 mm.

*Color.*—Varies from 2.5GY 5/6 to 2.5GY 5/8.

Flesh:

*Ripens.*—Evenly.

*Texture.*—Firm and meaty.

*Fibers.*—Few, small, tender.

*Firmness.*—Good, comparable to the commercial peach variety 'Rich Lady' (U.S. Plant Pat. No. 7,290).

*Aroma.*—Slight.

*Amydgalin.*—Undetected.

*Eating quality.*—Very good.

*Flavor.*—Very good, mild and sweet.

*Juice.*—Moderate amount, enhances flavor.

*Brix.*—Average 9.7°, varies slightly with amount of fruit per tree and climatic conditions.

*Color.*—Yellow, varies from 2.5Y 8/10 to 2.5Y 7/10.

*Pit cavity.*—Average length 36.7 mm. Average width 30.8 mm. Average depth 12.9 mm. Color varies frim 2.5Y 6/10 to 5R 3/10.

Skin:

*Thickness.*—Medium.

*Surface.*—Smooth.

*Pubescence.*—Moderate amount.

*Tendency to crack.*—None.

*Color.*—Ground color yellow, varies from 5Y 8/6 to 5Y 8/8. Overspread with 7.5R 4/8 to 7.5R 3/6.

*Tenacity.*—Tenacious to flesh.

*Astringency.*—Undetected.

Stone:

*Type.*—Clingstone.

*Size.*—Large. Average length 35.1 mm. Average width 27.3 mm. Average thickness 21.7 mm.

*Form.*—Obovoid.

*Base.*—Varies from round to flat.

*Apex.*—Pointed. Average length 2.1 mm.

*Surface.*—Pitted throughout, pits vary from round to elongated.

*Sides.*—Unequal, one side extending further from suture plane.

*Ridges.*—Relatively smooth, extending from base toward apex.

*Tendency to split.*—None.

*Color.*—Varies from 10YR 6/6 to 10YR 5/8 when dry.

Kernel:

*Size.*—Medium to large. Average length 18.0 mm. Average width 12.2 mm. Average depth 7.3 mm.

*Shape.*—Ovoid.

*Viability.*—Viable, complete embryo development.

*Skin.*—Color varies from 5Y 8.5/6 to 7.5Y 9/4 when dry.

Use: Dessert.

*Market*—Local and long distance.

Keeping quality: Good, held firm in cold storage at 38° to 42° F. for 2 weeks without internal breakdown of flesh or appreciable loss of flavor.

Shipping quality: Good, minimal skin scarring or flesh bruising during picking, packing and shipping trials.

Plant/fruit disease resistance/susceptibility: No specific testing for relative plant/fruit disease resistance/susceptibility has been designed. Under close observation during planting, growing and harvesting of fruit, under normal cultural and growing conditions near Modesto, Calif., no particular plant/fruit disease resistance or susceptibility has been observed. Any variety observed during indexing of plant characteristics with abnormal fungus, bacterial, virus or insect susceptibility is destroyed and eliminated from our breeding program.

The present new variety of peach tree, its flowers, foliage and fruit herein described may vary in slight detail due to climate, soil conditions and cultural practices under which the variety may be grown. The present description is that of the variety grown under the ecological conditions prevailing near Modesto, Calif.

The invention claimed is:

1. A new and distinct variety of peach tree (*Prunus persica*), substantially as illustrated and described.

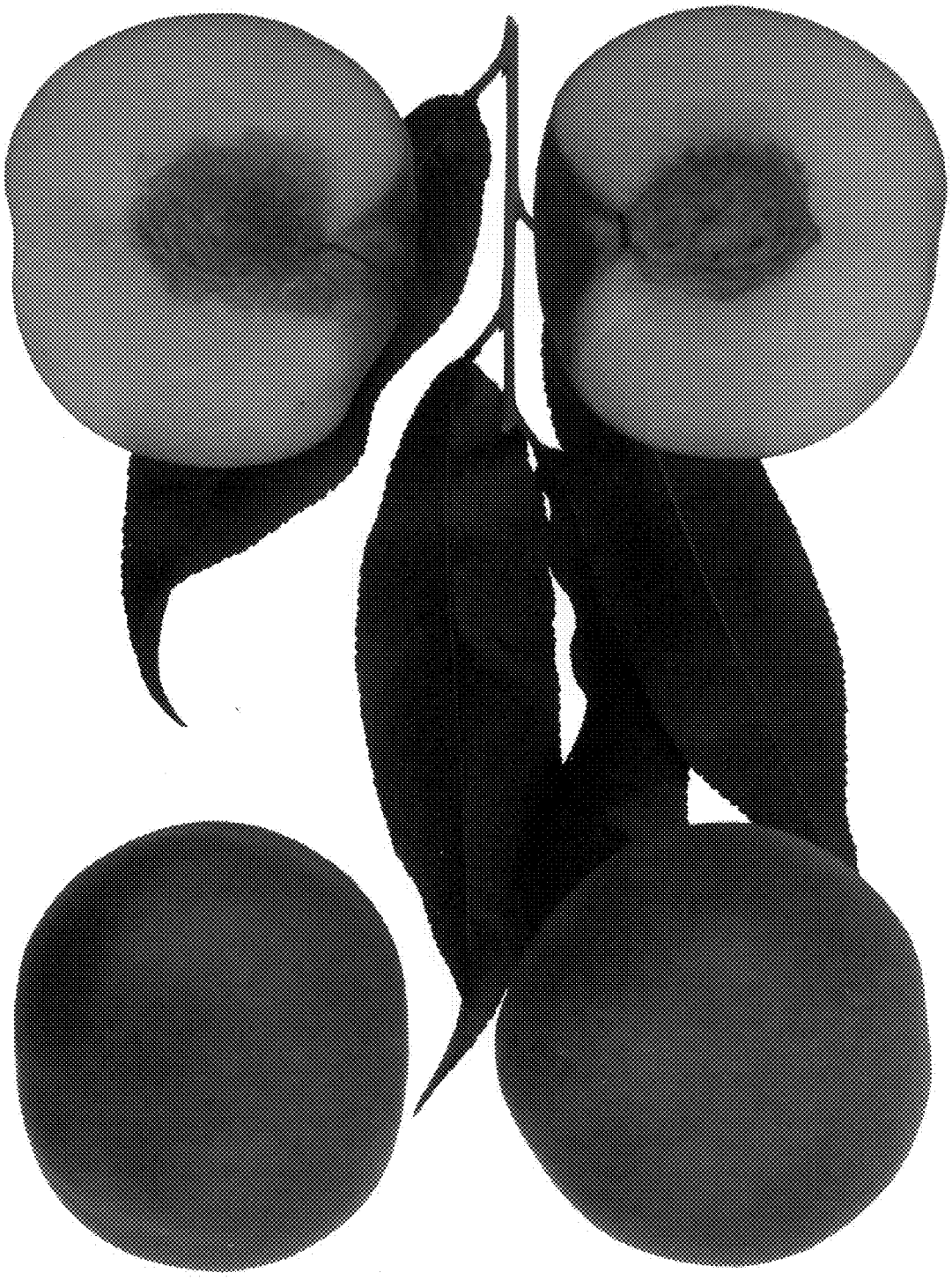

* * * * *